(12) United States Patent
Yamamoto et al.

(10) Patent No.: US 7,713,394 B2
(45) Date of Patent: May 11, 2010

(54) ELECTROPHORESIS APPARATUS USING CAPILLARY ARRAY AND SAMPLE PLATE ASSEMBLY USED THEREFOR

(75) Inventors: Shuhei Yamamoto, Hitachinaka (JP); Hiromi Yamashita, Ishioka (JP); Masatoshi Kitagawa, Mito (JP)

(73) Assignee: Hitachi, Ltd., Tokyo (JP)

( * ) Notice: Subject to any disclaimer, the term of this patent is extended or adjusted under 35 U.S.C. 154(b) by 1118 days.

(21) Appl. No.: 11/302,125

(22) Filed: Dec. 14, 2005

(65) Prior Publication Data

US 2006/0086613 A1    Apr. 27, 2006

Related U.S. Application Data

(63) Continuation of application No. 09/842,685, filed on Apr. 27, 2001, now Pat. No. 7,056,427.

(30) Foreign Application Priority Data

May 15, 2000    (JP) ............................. 2000-147496

(51) Int. Cl.
- *C02F 1/40* (2006.01)
- *B01J 19/12* (2006.01)
- *C25D 17/00* (2006.01)
- *B01D 57/02* (2006.01)
- *G01N 21/00* (2006.01)

(52) U.S. Cl. ................... 204/601; 204/193; 204/194; 204/451; 204/452; 204/453; 204/455; 204/603; 204/604; 204/605; 422/63; 422/64

(58) Field of Classification Search ............... 204/601, 204/193, 194, 451, 453, 452, 455, 603, 604, 204/605; 422/63, 64
See application file for complete search history.

(56) References Cited

U.S. PATENT DOCUMENTS

| | | | |
|---|---|---|---|
| 5,274,240 A | 12/1993 | Mathies et al. | |
| 5,366,608 A | 11/1994 | Kambara | |
| 5,384,024 A * | 1/1995 | Moring et al. | ............... 204/602 |
| 5,439,578 A | 8/1995 | Dovichi et al. | |
| 5,516,409 A | 5/1996 | Kambara | |
| 5,529,679 A | 6/1996 | Takahashi et al. | |
| 5,582,705 A | 12/1996 | Yeung et al. | |
| 5,730,850 A | 3/1998 | Kambara et al. | |
| 5,790,727 A | 8/1998 | Dhadwal et al. | |
| 5,916,428 A * | 6/1999 | Kane et al. | ................... 204/601 |
| 6,017,765 A | 1/2000 | Yamada et al. | |
| 6,203,760 B1 | 3/2001 | van der Plaats et al. | |
| 6,258,325 B1 | 7/2001 | Sanadi | |
| 6,365,024 B1 | 4/2002 | Li et al. | |
| 6,485,690 B1 | 11/2002 | Pfost et al. | |
| 6,495,104 B1 | 12/2002 | Unno et al. | |
| 7,390,390 B2 | 6/2008 | Yamamoto et al. | |

FOREIGN PATENT DOCUMENTS

| | | |
|---|---|---|
| EP | 0 431 251 A1 | 6/1991 |
| EP | 0 864 860 A1 | 9/1998 |
| JP | 6-324054 A | 11/1994 |
| JP | 9-325154 A | 12/1997 |
| JP | 2001-13152 A | 1/2001 |
| JP | 2001-99813 A | 4/2001 |
| WO | WO 98/52047 | 11/1998 |
| WO | WO 99/42819 A1 | 8/1999 |
| WO | WO 00/16085 | 3/2000 |

* cited by examiner

*Primary Examiner*—Ling-Siu Choi
*Assistant Examiner*—Monique Peets
(74) *Attorney, Agent, or Firm*—Dickstein Shapiro LLP

(57) ABSTRACT

A sample plate assembly for an electrophoresis apparatus including a tray at a sample supply portion of a capillary array, an adapter for the tray, a sample plate mounted on the adapter, a septer mounted on the sample plate and a septer holder mounted on the septer. Thereby, many number of samples can be automatically supplied to capillaries in a multi capillary array.

4 Claims, 9 Drawing Sheets

ELECTROPHORESIS APPARATUS USING CAPILLARY ARRAY AND SAMPLE PLATE ASSEMBLY USED THEREFOR

This is a continuation application of U.S. patent application Ser. No. 09/842,685, filed on Apr. 27, 2001, now U.S. Pat. No. 7,056,427 the entire disclosure of which is incorporated by reference herein.

BACKGROUND OF THE INVENTION

1. Field of the Invention

The present invention relates to an electrophoresis apparatus which separates and analyzes samples such as DNA and protein by making use of a plurality of capillaries and a sample plate assembly used therefor.

2. Conventional Art

An application technology in which an array is constituted by combining a plurality of capillaries, an electrophoresis medium and a sample to be separated or analyzed are supplied to the respective capillaries and moved therethrough to thereby separate and analyze the object sample is well known, wherein a sample such as DNA and protein marked by a fluorescent material is supplied to the capillaries. Such application technology is, for example, disclosed in U.S. Pat. Nos. 5,366,608, 5,529,679, 5,516,409, 5,730,850, 5,790,727, 5,582,705, 5,439,578 and 5,274,240. In view of a through-put of the separation and analysis, it is much more advantageous to use electrophoresis with multi capillaries rather than electrophoresis with a flat plate gel.

A capillary array electrophoresis apparatus is basically constituted by such as a capillary array, an excitation light system including a laser beam source, a light receiving optical system which detects fluorescence and a voltage application unit which causes electrophoresis. In such capillary array electrophoresis apparatus the capillary array is constituted by aligning a plurality of capillaries in a plane shape, and a laser beam is irradiated to the capillaries which are filled with a sample (fluorescent sample) marked by a fluorescent material in parallel direction with the capillary aligning direction, then, through the lens action of the capillaries the laser beam is condensed and the laser beam is irradiated to the fluorescent sample in all of the capillaries when the laser beam is irradiated, the fluorescent sample emits fluorescence. Through detection by the light receiving optical system of the fluorescence emitted from the fluorescent sample in a direction substantially perpendicular to the laser beam irradiation direction, the measurement of the sample is performed.

SUMMARY OF THE INVENTION

In order to automatically supply at least a sample to capillaries in a multi capillary array, a sampling device is used. An object of the present invention is to provide an electrophoresis apparatus which can perform separation and analysis of samples by supplying many samples continuously to the capillaries and a sample plate assembly used for the apparatus.

In an electrophoresis apparatus in which a sample marked by fluorescent material is separated in capillaries through electrophoresis by making use of a capillary array formed by a plurality of capillaries, fluorescence emission is caused by irradiation light to the sample and through detection of the fluorescence the sample is analyzed, the present invention provides an electrophoresis apparatus which comprises a sample plate assembly including two sets of a tray at a sample supply portion of the capillary array, an adapter for the tray, a sample plate mounted on the adapter, a septum mounted on the sample plate and a septum cover mounted on the septum, wherein two sample plates include respectively different numbers of wells, and the tray, the adapter, the septum and the septum holder in each set being adapted to the corresponding different sample plate. Further, the tray includes a sensor for discriminating the adapter, and thereby the sample plate assembly is correctly placed on the tray. Still further, the tray is designed to permit mounting a plurality of units thereon according to the sample plate assembly being mounted thereon and the respective trays are provided with a sensor which permits to judge whether the unit is correctly mounted.

Further, the present invention provides a sample plate assembly including two sets of a tray at a sample supply portion of the capillary array, an adapter for the tray, a sample plate mounted on the adapter, a septum mounted on the sample plate and a septum cover mounted on the septum, wherein two sample plates include respectively different numbers of wells, and the tray, the adapter, the septum and the septum holder in each set being adapted to the corresponding different sample plate.

DETAILED DESCRIPTION OF THE EMBODIMENTS

Figure 1:
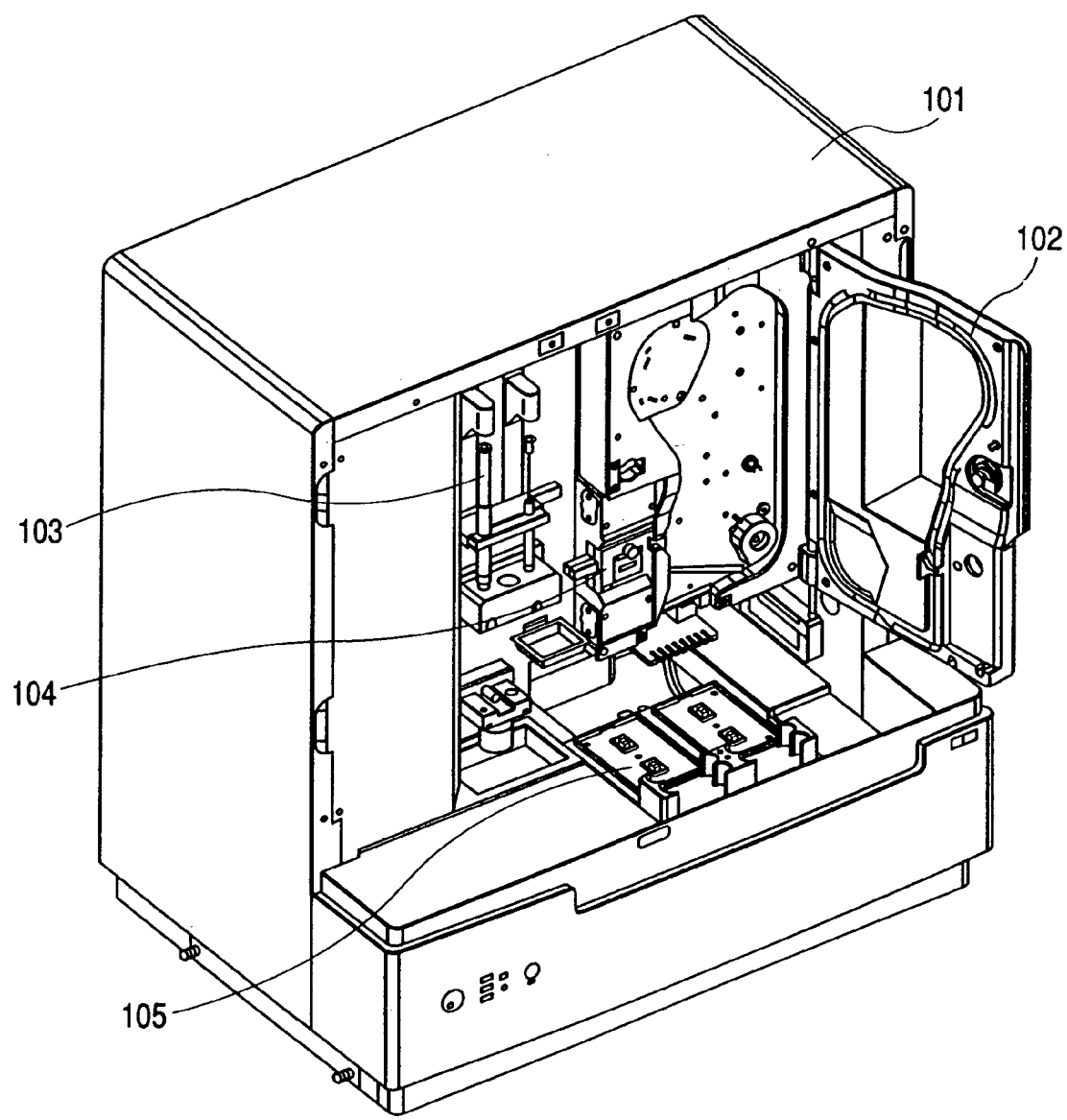
FIG. 1 is a perspective view showing an outlook of an electrophoresis apparatus according to the present invention wherein a door of a thermostatic oven is opened and no capillary array is attached thereto.

An electrophoresis apparatus according to the present invention will be explained with reference to FIGS. 1 through 4. As shown in FIG. 1, on a frame 101 of the electrophoresis apparatus a thermostatic oven 102 including a Peltier element and permitting temperature control, a detector portion 104 and a gel pump which supplies an electrophoresis medium to capillaries in a capillary array are provided. The capillary array is disposed in a space of the thermostatic oven and a sample plate assembly is attached to a tray 105.

Figure 2:
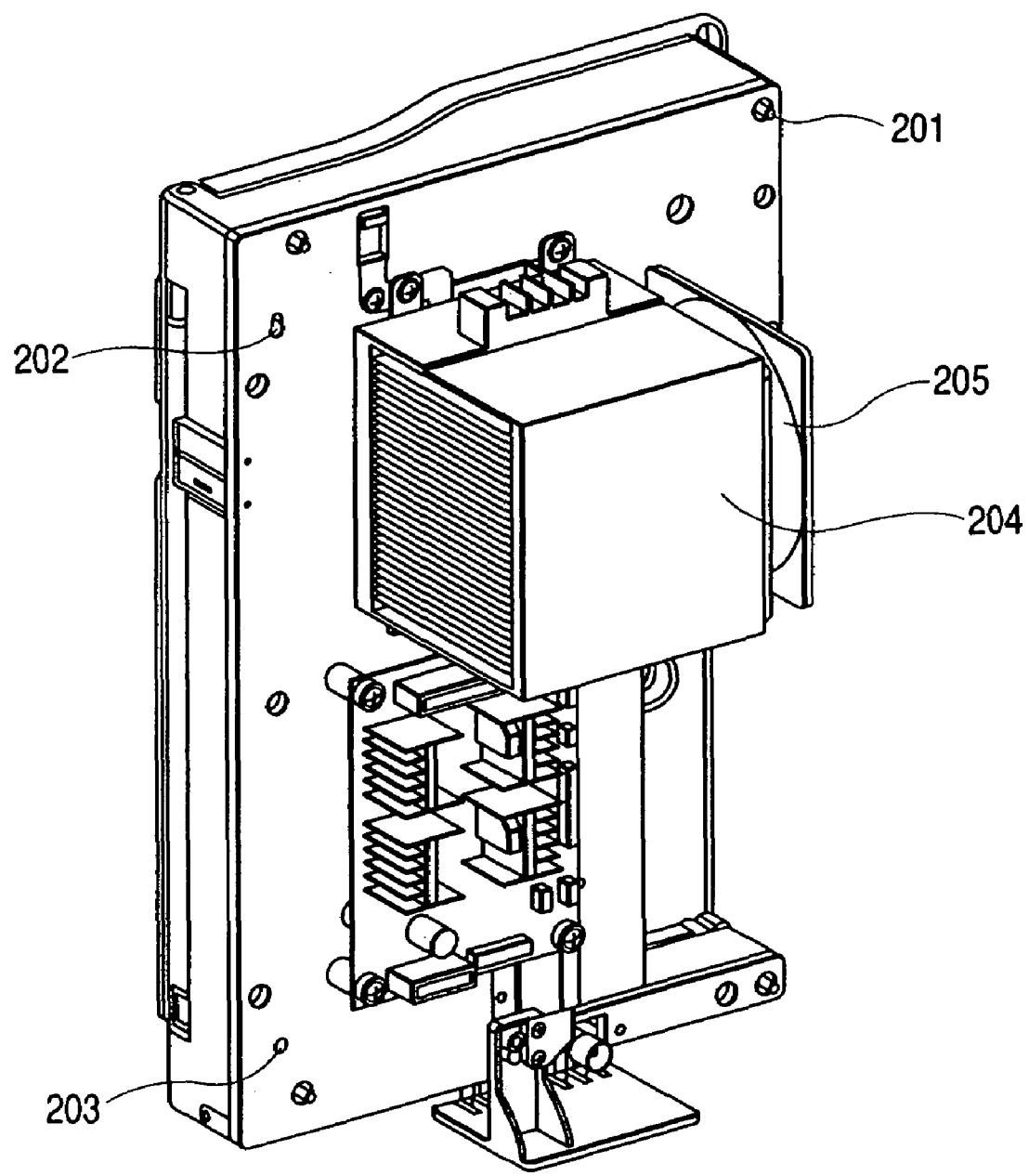
FIG. 2 is a perspective view showing a back side structure of the thermostatic oven in FIG. 1.

FIG. 2 shows a back face of the thermostatic oven 102. At the back face of the thermostatic oven 102 Peltier heat radiation fins 204 and Peltier heat radiation fan 205 are provided and further the thermostatic oven 102 is provided with means for controlling temperature therein properly.

Figure 3:
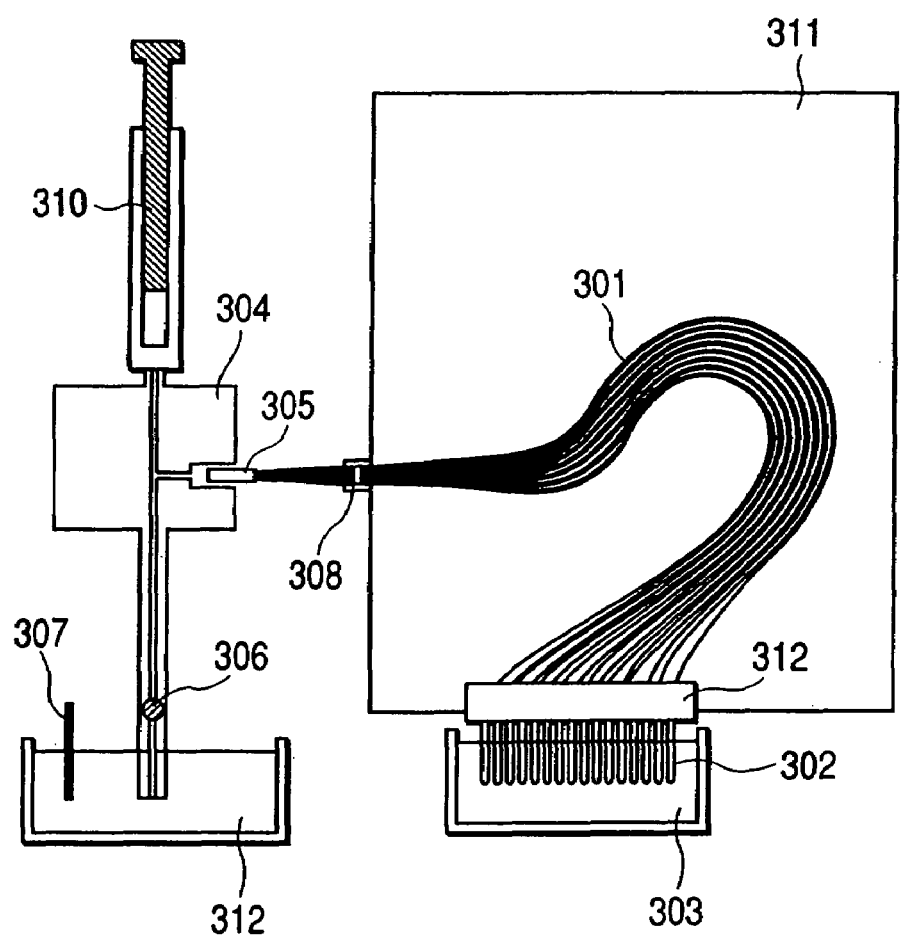
FIG. 3 is a schematic diagram showing a relationship between such as a thermostatic oven and a pump unit in a capillary unit according to the present invention.

As shown in FIG. 3, a capillary array 301 is attached to a thermostatic oven 311 and a sample supply side 302 of the capillary array 301 is immersed into a buffer vessel 303 via a capillary array holder 312. The sample supply side 302 is provided with an electrode.

A gel supply side 305 of the capillary array 301 is connected to a gel pump system 304 and the gel is supplied from a reservoir 312 by a syringe 310. Another electrode 307 is attached to the reservoir 312. A detection portion 308 of fluorescence generated from a sample marked by fluorescent material which is separated by electrophoresis in the capillaries is disposed outside the space in the thermostatic oven 311.

An entire operation of an electrophoresis apparatus using a capillary array according to the present invention will be explained with reference to FIG. 4. The capillary array according to the present invention includes a buffer liquid injection port 430 which is formed by bundling one ends of the plurality of capillaries and is set to a buffer liquid container 417 for injecting buffer liquid and a part of coating of the capillaries are removed. The coating removed portions of the capillaries are aligned in a plane shape and the portion where at least a part of the plurality of capillaries is aligned in plane shape is held on a holder substrate. The holder substrate is provided with a window at a portion corresponding to the coating removed portions of the respective capillaries through which detection light 435 passes. The holder substrate includes a light detection portion provided with a light shielding region defining the window through which the detection light 435 passes.

Figure 4:
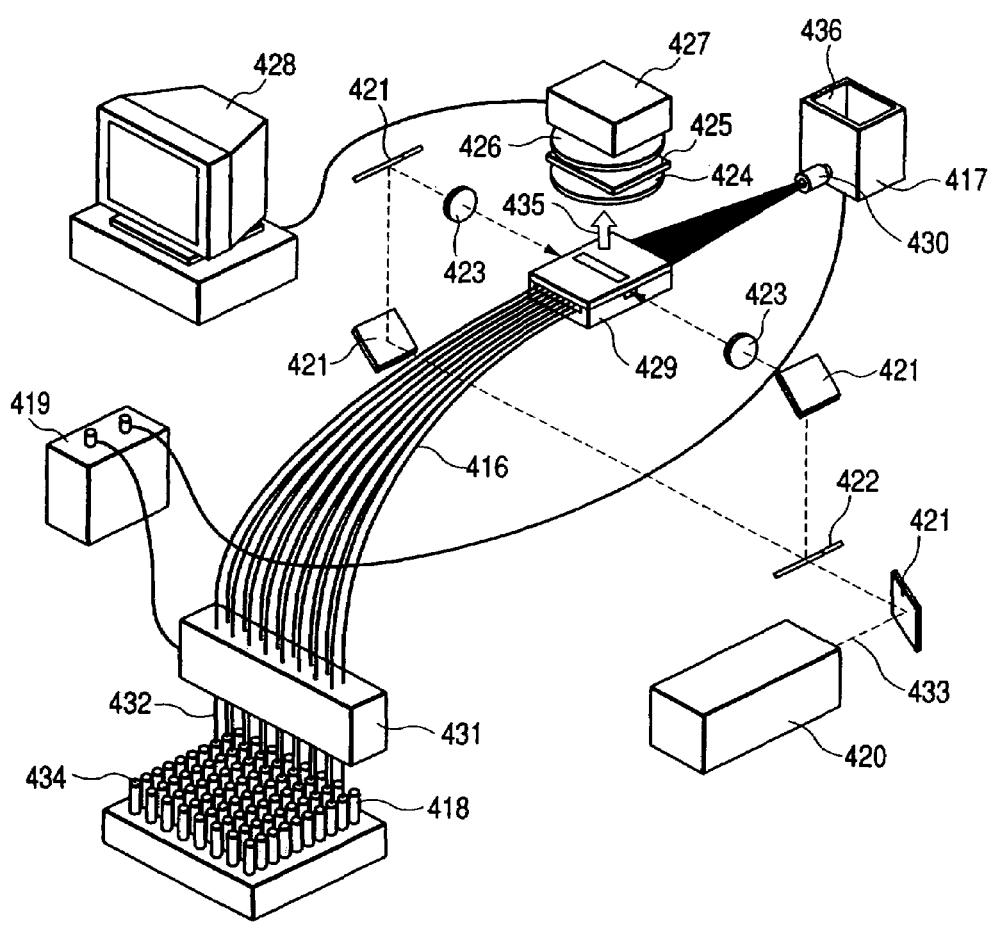
FIG. 4 is a schematic diagram for explaining an entire structure of an electrophoresis apparatus according to the present invention.

In FIG. 4, at the other ends of the plurality of capillaries an introduction portion 432 is constituted through which a sample marked by a fluorescent material is introduced into the capillary array and an electrode for applying a voltage necessary for electrophoresis on the respective capillaries is provided near the top ends of the fluorescent sample introduction portion 432. The voltage necessary for the electrophoresis is applied from a power source 419 between the electrode provided at a capillary array holder 431 and a reservoir 417 for supplying an electrophoresis medium.

As shown in FIG. 4, the capillary array electrophoresis apparatus is constituted by such as a sample measurement portion 416, a buffer liquid container 417, a fluorescent sample container 418, a high voltage power source 419, a laser beam source 420, a mirror 421, a beam splitter 422, a condenser lens 423, a first lens 424, an optical filter and image dividing prism 425, a first lens 426, a CCD camera 427, and a processor unit 428. Further, the sample measurement portion 416 is constituted by such as capillaries, a light detection portion 429, a buffer liquid injection portion port 430 and a conductive fluorescent sample injection port 432.

Now, the operation of the capillary array electrophoresis apparatus will be explained. As shown in FIG. 4, laser beam 433 generated from the laser beam source 420 is divided into two parts by the beam splitter 422 and the advancing direction thereof is altered by the mirror 421. The laser beam 433 is condensed by the condenser lens 423 and is irradiated to the capillaries from a direction in parallel with the plane where the capillaries are aligned. Since the inside of the capillaries is filled with a sample (fluorescent sample 434) marked by a fluorescent material, when the laser beam 433 is irradiated to the fluorescent sample 434, the fluorescent sample 434 emits fluorescence. The detection of the fluorescence 435 is performed in such a manner that the fluorescence 435 emitted substantially in perpendicular direction with respect to the capillary alignment plane is converted into parallel light and is image-divided by the optical filter and image dividing prism 425, thereafter, an image is formed on the CCD camera 427 by the second lens 426 to thereby detect the fluorescence. The detected measurement data are processed by the processor unit 428.

In FIG. 4, the laser beam 433 is irradiated from both sides of light detection portion 429, however, the laser beam 433 can be irradiated from one side thereof. The light receiving optical system is not limited to the structure as shown in FIG. 4. Further, the number of the constituting capillaries is not limited to 16 pieces and the structure of the buffer liquid injection port 430 and the conductive fluorescent sample injection port 432 is not also limited to those shown in FIG. 4.

Now, the operation sequence of the capillary array electrophoresis apparatus will be explained. The buffer liquid 436 contained in the buffer liquid container 417 is injected into the capillaries from the buffer liquid injection port 430. Then, the conductive fluorescent sample injection port 432 is immersed into the fluorescent sample container 418 filled with the fluorescent sample 434 to inject the fluorescent sample 434 into the capillaries. Thereafter, the conductive fluorescent sample injection port 432 is immersed into another buffer liquid container (not shown) containing a buffer liquid and a high voltage is applied between the buffer liquid injection port 430 and the fluorescent sample injection port 432 from the high voltage power source 419 to cause electrophoresis in the capillaries. Since the moving speed in the electrophoresis is proportional to the magnitude of electric charge of the molecules and is antiproportional to the size of the molecules, the fluorescent sample 434 is separated. Through the continuous application of the high voltage for a long time the electrophoresis is caused for a long time and the fluorescence 435 emitted during the electrophoresis is continuously measured.

The sample introduction portion 432 is structured by inserting capillaries into stainless tubes. Respective stainless tubes are soldered to an electrode plate with a protective cover and through application of a voltage to the connecting portion 431, the voltage is applied all of the stainless tubes. As has been explained, since the capillary array itself is provided with all necessary functions including the buffer liquid injection port 430 attached to the buffer liquid container 417, a light detection portion 429 in which laser beam is irradiated and the fluorescence is detected and the sample introduction portion 432 through which the fluorescent sample 434 is introduced and a voltage necessary for electrophoresis is applied thereto, when an exchange of the capillary array is required, the capillary array can be exchanged with a very easy handling.

Further, the top of the fluorescent sample injection port 432 is sealed by an adhesive so as to prevent carry over of such as the sample. A kind of the adhesive used is an epoxy series adhesive and the same is fully cured so as not to affect the electrophoresis. Gaps between capillaries and insertion portions therefor in the sample introduction portion 432 and between the fluorescent sample injection port 432 and the protective covers are sealed with an adhesive. Thereby, a possible electric insulation reduction is prevented which can be caused when water contained in the sample and the buffer liquid penetrates into the covers of the stainless tubes.

When once detaching the capillary array from the apparatus and storing the same after measurement of the sample, a dry preventive container cover (not shown) is attached so as not to dry the buffer liquid 436. The container cover is a dry preventive cover for the sample introduction portion 432. The container cover is attached to the sample introduction portion 432 while charging pure water therein. The container cover is provided with an O ring to thereby prevent a possible drying. It is also effective to provide a dry protective cap (not shown) for the buffer liquid injection port 430. In such instance the cap is set onto the buffer liquid injection port 430 under the condition in which a small amount of pure water is likely filled therein. When the inner diameter of the cap is determined to be smaller than outer diameter of the buffer liquid injection port 430 by about 5-15% to thereby prevent a possible drying. As a material of the cap, silicon rubber is preferable, because the silicon rubber causes no adverse effect to the buffer liquid and the electrophoresis. These cover and cap also work to protect the top end thereof and to prevent contamination thereof, when shipping the capillary array to a customer.

Each of the capillaries used in the capillary array as explained above is a fused quartz tube having inner diameter of 50±10 μm and outer diameter of 340±20 μm. Since the fused quartz tube itself breaks very easily, a polyimide coating having thickness of 15±5μm is applied on the surface of the capillary. In view of limiting amount of fluorescent sample 434 it is desirable to reduce the inner diameter of the capillary, however, on the other hand in view of a concave lens effect due to refractive index difference between the fluorescent sample 434 and fused quartz, the capillary having a too small inner diameter makes the measurement difficult. Therefore, the inner diameter of 50~100 μm is preferable for the fused quartz tube. Further, in order to suppress the above refractive index difference it is preferable that the outer diameter of the fused quartz tube is small, however, a too small outer diameter makes assembly thereof difficult because of static electricity, therefore, the outer diameter of 250~350 μm is preferable for the fused quartz tube. The coating material for the capillary is not limited to the polyimide, a material having an equivalent electrical insulation and other properties as those of polyimide can be used.

A sample plate assembly used for the auto sampler according to the present invention is formed into a four layer structure by laminating a plate adapter, a plate, a septum and a septum holder. The above unit is mounted on a tray of the electrophoresis apparatus according to the present invention. In order to reduce load for a person performing analysis, the analysis is performed by charging a sample to be analyzed into a marketed microtiter plate which is marketed from many manufacturers. These microtiter plates respectively include the corresponding adapters and any type of microtiter plates can be attached to an auto sampler. These microtiter plates can be classified into two kinds depending on the number of samples which can be charged into one plate.

One of the microtiter plates includes wells of 8×12=96 holes for introducing and holding samples into the plate and another microfiter plates includes wells of 16×24=384 holes. Sample plates referred to hereinbelow indicate these plates and the former sample plate will be referred to as a 96 sample plate and the latter as a 384 sample plate. Since in the electrophoresis apparatus according to the present invention two sets of the above sample plates can be mounted at the same time, a continuous analysis of 384×2=768 samples in maximum can be performed.

Figure 5:
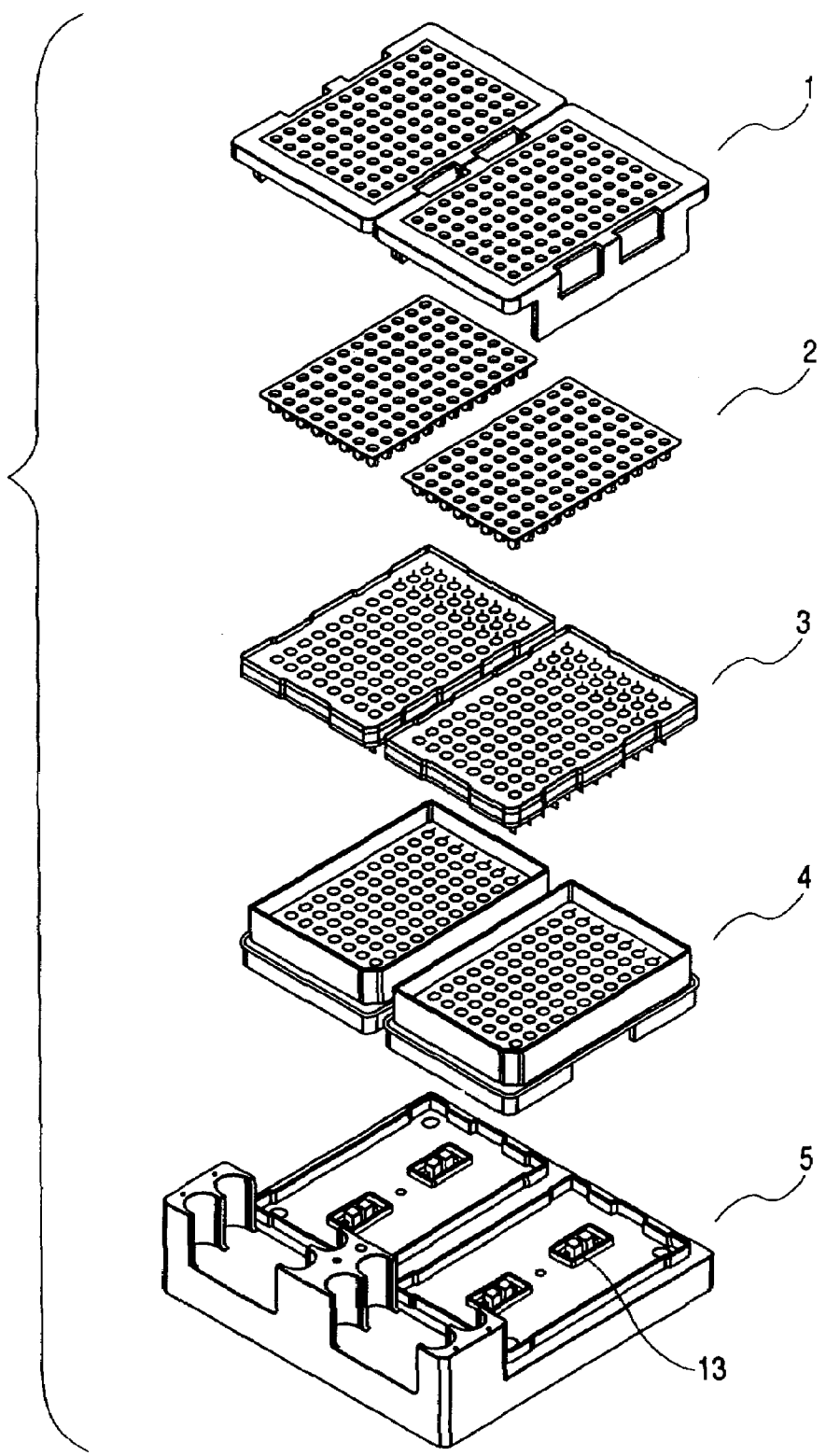
FIG. 5 is an exploded perspective view showing a structure of an auto sampler and a tray according to the present invention.

FIG. 5 is a sample plate showing in an exploded manner when two 96 sample plates are set to an auto sampler. After a sample plate 3 is assembled with a plate adapter 4, a septum 2 and a septum holder 1 (hereinbelow, will be called as well plate assembly, see FIG. 6), and the assembly is set to a tray 5 for the auto sampler. The plate adapter 4 is a base for setting the sample plate 3 onto the tray 5 for the auto sampler.

The septum 2 has a function of preventing evaporation of the samples and further serves to function of wiping off such as sample deposited at the top end of the capillaries. In the electrophoresis apparatus according to the present invention, a number of analyses per day for a standard sequence analysis is set to be 96 samples, therefore, with the present apparatus which permits mounting of two 96 hole sample plates at the same time, an automatic operation with no person can be performed in two days. Therefore, the evaporation of such as the sample and buffer solution is an important problem. Through fitting the septum 2 onto the sample plate 3 the evaporation of such as samples is prevented.

Further, the top end portion of the capillary array performing electrophoresis is immersed during the sample analysis into the sample, buffer liquid and water depending on purposes of analysis. The gel causing the sample in the capillaries electrophoresis is exchanged for every electrophoresis, therefore, in such instance the top ends of the capillaries are immersed in a waste liquid vessel (water) in order to receive the exhaust gel from the top ends of the capillaries. Thereafter, in order to introduce the sample into the capillaries, the end terminals thereof together with the electrode provided at the top end of the capillary array are inserted into the sample, and a high voltage is applied to the electrode and the sample is introduced into the respective capillaries. Further, when performing electrophoresis, the top ends of the capillary array are immersed into the buffer vessel so as to prevent electrical discharge during the high voltage application as well as to cause the sample electrophoresis.

When the sample plate assembly moves between the waste liquid vessel, the sample and the buffer vessel, the top ends of capillaries are immersed once or a plurality of times in a cleaning vessel (water) for cleaning so as to prevent mixing of such as sample and buffer liquid deposited at the top ends of the capillaries into other solution. The septum 2 is made of silicon rubber and is provided with projections so that the top ends thereof are inserted into respective wells in the sample plate 3, and cuttings are provided at the top ends thereof so as to permit passing of the capillary top ends therethrough. When the auto sampler moves, the capillaries once and always lower to a height so as not to touch the auto sampler, therefore, every time when the capillaries lower, water, sample and buffer liquid deposited at the top ends of the capillaries are wiped off by these cuttings, thereby, mixture of these to other solution is suppressed in minimum.

The septum holder 1 is a holder for securing the well plate and septum to the adapter.

Now, the structure of the septum holder (positioning guide) will be explained.

Figure 6:
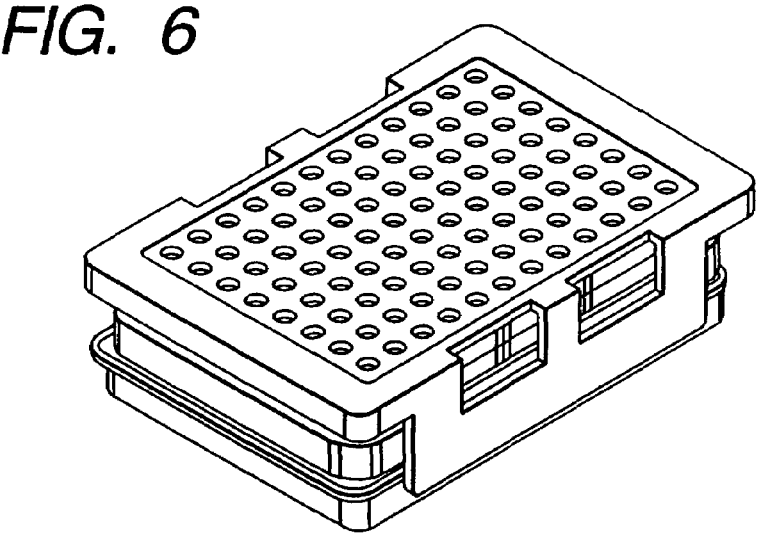
FIG. 6 is a perspective view showing an assembled state of an auto sampler according to the present invention.
Figure 7:
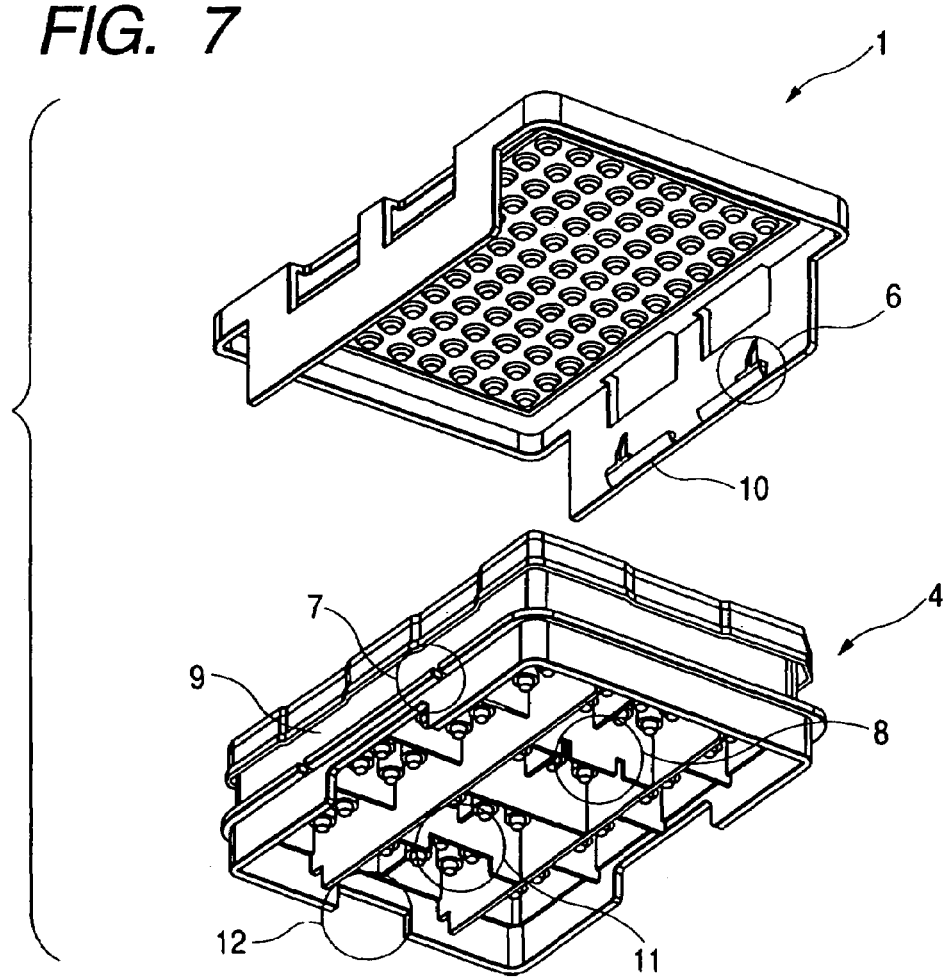
FIG. 7 is a perspective view for explaining assembling structure of a septum holder, a septum, a sample plate and a sample plate adapter.

FIG. 6 shows a state when the septum holder 1, the septum 2, the sample plate 3 and the plate adapter 4 are assembled. FIG. 7 shows when only the septum holder 1 is detached from the sample plate assembly. The septum holder 1 is a member for securing the septum 2 and the sample plate 3 to the plate adapter 4. Further, since the sample plate 3 is used in a heat processing called PCR (Polymerase Chain Reaction) representing a preprocessing of the sample and is possibly deformed by the heat processing depending on the conditions, the septum holder 1 serves to reform the deformed sample plate 3 and to secure correctly to the adapter 4.

In order to reduce time for a person performing analysis, the septum holder 1 is configured in a simple structure, in that the septum holder 1 can be secured to the adapter 4 only by fitting to two sets of pawls 10 provided at respective right and left sides to the flanges 9 of the adapter 4. Therefore, it is possible that the septum holder 1 can be fitted to the plate adapter 4, while being offset in longitudinal direction. If the septum holder 1 is erroneously secured to the plate adapter 4, the holes in the septum holder 1 through which capillaries pass do not align the wells in the sample plate 3 which breaks the capillaries. In order to prevent such possibility, there are provided projections 6 at the portions where the four pawls 10 are formed at the side of the septum holder 1 and if the projections 6 do not match with guides 7 at the side of the plate adapter 4, the pawls 10 can not fit to the flange 9 and the septum holder 1 can not be attached to the plate adapter 4. With this measure, a person performing analysis can attach the septum holder 1 to the plate adapter 4 without special attention, and further an attachment to an erroneous position never occurs.

The auto sampler according to the present invention can be adapted to different plates (having different height) by making use of the adapter. Among the sample plates used in the electrophoresis apparatus according to the present invention, even with sample plates having the same 96 wells a plurality of types are marketed, and such as the shape, size and well depth thereof are different depending on the manufacturers.

For example, when the minimum sample amount for the electrophoresis apparatus according to the present invention is set at 10 μl, the height from the bottom of the well to the sample liquid surface for one of marketed 96 sample plates is about 2.5 mm, therefore, in order to surely introduce the sample into the capillary, the capillary has to be inserted to the height of about 1 mm from the bottom of the well. However, the height of the well bottom greatly varies depending on the sample plates marketed, therefore, if the sample plates are used without careful discrimination, there arises a problem that the top end of the capillary may touch the bottom of the well to break the capillaries or may not reach the sample to thereby fail the introduction of the sample into the capillary.

Therefore, in order to correct such-as the bottom height and the position of center axis of the well in the sample plates of respective manufacturers, plate adapters corresponding to respective sample plates are prepared and are used in combination with the respective sample plates, therefore, the center axis and the bottom height of the well for any sample plates having 96 wells are set equal with respect to tray 5 in the auto sampler. Thus, it is sufficient if the auto sampler only discriminates number of wells in that 96 or 384, of the sample plate assembly mounted thereon and determines control method depending on the discrimination, the auto sampler can always be moved for any type of 96 sample plates mounted under the same control method.

Further, it is difficult to separate at a glance the 96 well sample plates of respective manufacturers depending on the configurations thereof, therefore, in order not to be attached to a wrong plate adapter or in a wrong direction, a measure is taken for the respective plate adapters. For example, in the case of the sample plate 3 as shown in FIG. 5, one of the four corners in the sample plate is cut off. The direction and size of the cut off vary depending on the sample plates of respective manufacturers, and the plate adapter 4 is also configured so as to adapt the same, therefore, it is prevented to attach a sample plate to a wrong plate adapter or in a wrong direction.

The auto sampler according to the present invention can be adapted to 96/384 well sample plates with an identical structure. Any two sets of the plate adapters for 96 well sample plate and the plate adapters for 384 well sample plate can be attached to the tray 5 as shown in FIG. 5, and further depending on purposes of a person performing analysis the combination thereof can be freely selected.

The electrophoresis apparatus according to the present invention can automatically discriminate the 96 plate and the 384 plate. As illustrated in FIG. 5, the tray 5 is provided with four photo diodes 13 in total, in that two photo diodes 13 to each sample plate assembly. In corresponding thereto and as illustrated in FIG. 7, the plate adapter 4 is provided with at the back side thereof (at the side of the tray 5) a light shielding plate 8 and a first cut-out 11, and when the plate adapter 4 is attached to the tray 5, the light shielding plate 8 interrupts light from one of two photo diodes 13.

The positional relationship between the light shielding plate 8 and the first cut-out 11 is inverted with respect to the plate adapter for 96 well sample plate and the plate adapter for 384 well sample plate, therefore, when the plate adapter 4 is attached to the tray 5 and signals from the two photo diodes 13 are compared, it is possible to discriminate whether the attached plate adapter is for the 96 well sample plate or for the 384 well sample plate. Further, with a second cut-out 12 as shown in FIG. 7 the plate adapter 4 can be attached to the tray 5 in one direction, therefore, if the plate adapter 4 is forcedly attached in a wrong direction, the light shielding plate can not interrupt lights from the both photo diodes 13. There are no chance to fail discrimination between the 96 well plate and the 384 well plate. With this function, a person performing analysis can set a sample plate without caring the kind thereof to the auto sampler to start the analysis, therefore, the time is saved for the person performing the analysis and a fear of causing unnecessary errors is avoided.

Figure 8A:
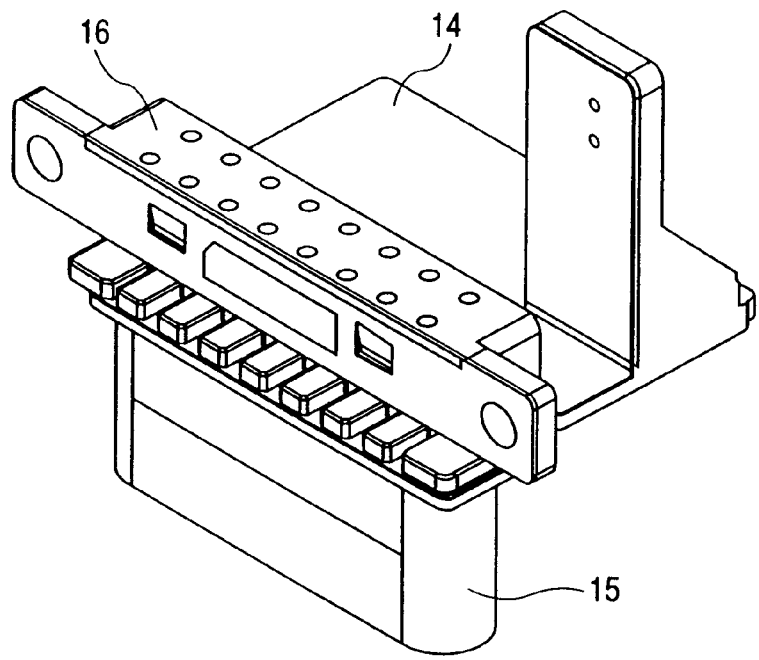
FIGS. 8A and 8B are perspective views showing a relationship between a stopper plate, a capillary array holder and a buffer plate which are attached to a thermostatic oven.
Figure 8B:
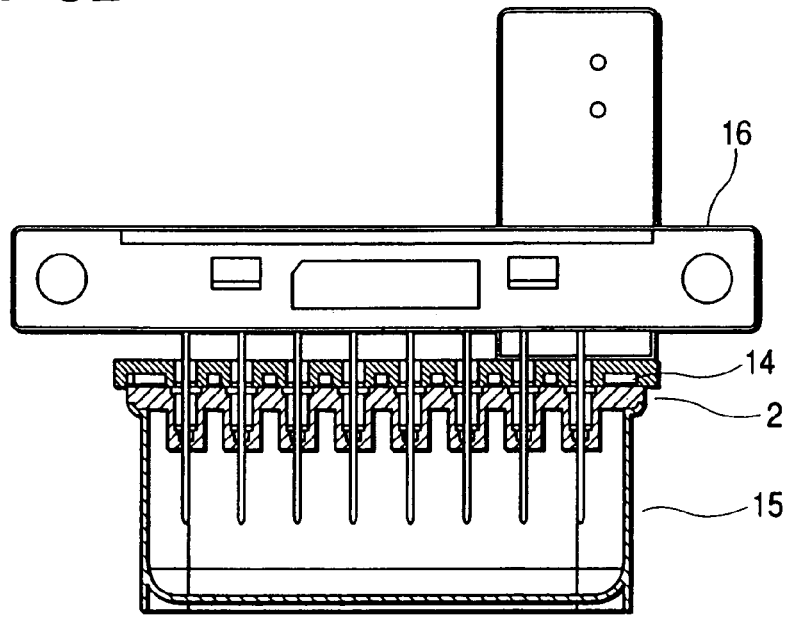

The auto sampler according to the present invention is provided with a stopper plate having a structure including an electrical discharge preventing measure. FIGS. 8A and 8B show in skeleton diagrams a manner where the capillary array 16 is inserted into a buffer vessel. In order to draw out the capillary array from the state where the capillary array is inserted into such as the sample plate assembly and the buffer vessel, when the auto sampler is moved down, there may arise a problem that the septum attached on such as the sample plate assembly and the buffer vessel can not be drawn out completely from the capillary array because of the friction force caused between the septum and 16 pieces of capillaries and under such condition the auto sampler starts to move in the X Y direction.

For preventing the above, in the present apparatus a stopper plate 14 as shown in FIGS. 8A and 8B is attached to an oven unit which is located above the auto sampler and to which the capillary array is attached. A spring is attached to the stopper plate 14 and under a normal condition the stopper plate 14 is adjusted so that the bottom face thereof positions at the same height as the top end of the capillary array.

Now, when the, capillary array is inserted into such as the sample plate and the buffer vessel, the stopper plate 14 is shifted upward due to the upward movement of the auto sampler, therefore, the stopper plate 14 pushes down the sample plate assembly and the buffer vessel by a larger spring force than the friction force. Thereby, when the auto sampler starts the downward movement, the stopper plate 14 always pushes down the sample plate assembly and the buffer vessel, there are no chances that such as the septum remains at the capillary array.

Further, the bottom face of the stopper plate 14, namely the face which contacts to such as sample plate assembly and the buffer vessel is structured not to be flat but uneven as shown in a cross section in FIG. 8B so as to reduce a contact face between the bottom face of the stopper plate 14 and the septum 2. If the bottom face of the stopper plate 14 is flat and when liquid such as water is deposited on the surface of the septum 2, the liquid spreads over the bottom face of the stopper plate 14 and it is possible that a high voltage applied to the capillary array can be discharged to a box body of the apparatus located near the stopper plate 14 through the liquid along the surface of the stopper plate 14 which is originally a plastic made insulative body. However, when the bottom face of the stopper plate 14 is structured uneven as shown in FIG. 8B, even if liquid is deposited on the surface of the septum 2, since the effect of spreading the liquid by the stopper plate 14 is reduced and further the creeping distance to the box body of the apparatus is prolonged, the possible electrical discharge from the capillary array to the box body of the apparatus can be prevented.

The auto sampler for the electrophoresis according to the present invention does not drop even when the power source is turned off, but can be pushed down manually. During analysis of a sample when the gel in the capillaries is dried, the introduction of the sample and the electrophoresis are disturbed. However, the top end portion of the capillary array which is subjected to the fear of drying is immersed in a liquid such as the sample and the buffer liquid substantially all the time during the analysis, although during the movement of the auto sampler between wells the top ends of the capillaries are exposed to the outer atmosphere, the exposed time is very short such as a few seconds, the gel in the capillaries does not generally dry during an analysis. Further, after completing an analysis or when interrupting analysis because of error detection, the top ends of the capillaries wait while being immersed in the buffer liquid, therefore, the gel at the top ends of the capillaries never dries before the subsequent analysis.

For the drive of the auto sampler, a drive scheme in combination of a stepping motor and a ball screw is basically employed, and during the time when the power source is made for the apparatus the stepping motor is always placed under an excitation condition, therefore, after completing an analysis, a condition that the capillaries are inserted into the buffer vessel, in other words the condition in which the auto sampler is shifted upward, can be maintained. However, sometimes it is desired to break the power source of the apparatus, because it is presumed to be long to the subsequent analysis or a person performing the analysis wants to interrupt the power source of the apparatus during an analysis for some reason, it is necessary that the auto sampler holds the position (the height in Z direction) before the power source is interrupted even under a condition where the power source of the apparatus is not made, in other words under the condition that the stepping motor is not excited.

On the other hand, when it is desired to remove the capillaries from the apparatus after the power source is interrupted, it is difficult to remove the capillaries if the capillaries are kept at the position where the capillaries are immersed in the buffer liquid, the auto sampler has to be pushed down manually to the height which permits the removal of the capillary array. Further, when the auto sampler can not operate normally because of occurrence of an abnormality, it is conceived necessary that the auto sampler is moved manually after interrupting the power source of the apparatus. For this reason, after the power source of the apparatus is interrupted, namely even under the condition that the stepping motor is not excited, the auto sampler always has to be kept at a predetermined position and if required the auto sampler can be moved manually by a person himself performing the analysis or by a person himself performing maintenance and inspection.

Figure 9:
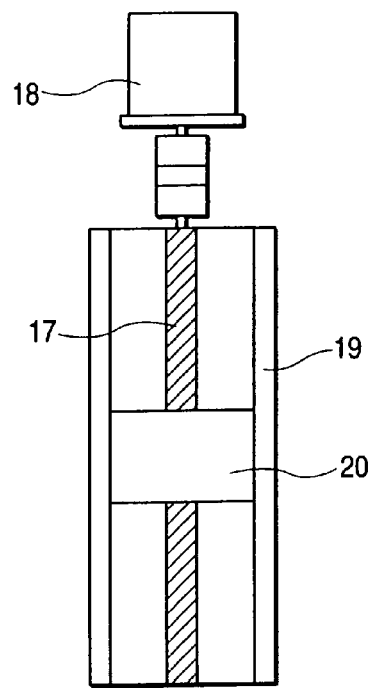
FIG. 9 is a schematic cross sectional view for explaining a drive mechanism of an auto sampler according to the present invention.

FIG. 9 is a skeleton diagram showing the drive scheme using a ball screw and a stepping motor. Since the X Y axis is the horizontal axis, even when the stepping motor is placed under no exciting condition the auto sampler never moves unless an external force is applied thereto, therefore, Z axis, in that the vertical axis, is exemplified herein in which direction a possibility of dropping is included. When assuming that a shaft diameter of the ball screw 17 is as $D_B$[m], a pitch of the ball screw 17 is as $P_B$[m], a total weight of a table and a work attached to the table is as W[N] and an internal friction coefficient of a prepressurized nut is as $\mu_0$, a force Fa[n] acting to the table 20 and tending to drop downward can be expressed as follows;

$$Fa = W \times \sin(\arctan(P_B/D_B \times \pi))[N] \quad (1)$$

and the total friction force F[N] acting to the table can be expressed as follows;

$$F = -\mu_0 \times W \times \cos(\arctan(P_B/D_B \times \pi))[N] \quad (2)$$

Accordingly, a condition where the table 20 and the work never drop downward even when the stepping motor is in a non-excited condition is as follows;

$$|Fa| < |F| \quad (3)$$

Now, as an inherent force which works so as not to drop the table, there is, for example, a detent torque (static torque at the time of no excitation) of the stepping motor, however, such torque is very small with respect to the forces now concerned and no substantial contribution to the above inequation (3) is considered, therefore, the inclusion thereof is omitted. In the present auto sampler, since $|Fa| \approx 11.4$[N], the above inequation is satisfied, therefore, the auto sampler never drops even under the condition that the stepping motor is placed under no excitation condition. Further, if the auto sampler is pushed downward with a force more than $|F| - |Fa| \approx 7$[N], the auto sampler can be easily pushed down. The relationship with regard to magnitudes of the forces expressed by the equations (1) and (2) can be determined by the pitch $P_B$ of the ball screw and the shaft diameter $D_B$ of the ball screw. The shaft diameter $D_B$ of the ball screw is determined in advance in view of the structure of the auto sampler and the required mechanical strength thereof so that alternation thereof is difficult, however, the pitch $P_B$ of the ball screw can be selected with comparatively a large tolerance if such as drive speed of the auto sampler and the operating condition of the stepping motor are properly adjusted, therefore, the inequation (3) can be realized easily.

The auto sampler according to the present invention makes use of a position guide (reference surface) at the time of assembly. When 384 well sample plate is used, the diameter of capillary insertion port in the sample plate assembly minimizes and the inner diameter of the septum holder in this instance is 2.3 mm. Since the outer diameter of the capillary including the electrode thereof is 0.71 mm, in order that a single capillary can be inserted into a well without touching the inner wall of the septum holder, the distance between the center axis of the capillary and the center axis of the well in the X Y plane is required to be less than about 0.8 mm.

Further, in the present apparatus which can perform a continuous measurement to the maximum of 786 samples, the auto sampler moves to sample positions in the maximum of 48 points, therefore, if the orthogonality of X and Y axes of the auto sampler offsets, there arises a problem that even when the capillaries can be inserted into the wells without troubles at a certain sample position, the capillaries touch to the septum holder at another sample position.

In view of the above problem, a high orthogonality with regard to X, Y and Z axes is required at the time of assembly of the auto sampler, therefore, in order to reduce time for the assembly as much as possible, all of the parts relating to the orthogonality with regard to X, Y and Z axes are provided with reference planes. Therefore, it is simply enough to assemble the same while matching the respective reference planes with each other. Thereby, the time required for the assembly and adjustment thereafter is greatly reduced, and further, such as parts exchange during maintenance can be performed easily.

In the electrophoresis apparatus according to the present invention positioning pins are provided for the auto sampler and the oven unit, a system is constituted which automatically reproduces their relative positions during the exchange of the unit.

The orthogonality of the auto sampler with regard to X, Y and Z axes has already been explained, the positional accuracy required for the present apparatus is further complex which uses a capillary array constituted by 16 pieces of capillaries. The capillaries are aligned in a grid shape of 2×8 at the sample introduction portion of the capillary array, therefore, even if the orthogonality of the auto sampler with regard to X, Y and Z axes is highly accurate, if the grid axes of the capillaries aligned in a grid shape are not in parallel with the X, Y and Z axes, it is not certain that all of the 16 pieces of capillaries can be inserted into the corresponding wells without trouble.

Although the sample introduction side of the capillary array is attached to the oven unit, if the capillary array is always correctly attached to the oven unit, the positional relationship between the capillary array and the auto sampler is determined by the positional relationship between the oven unit and the auto sampler. The positional relationship between the oven unit and the auto sampler can be satisfactorily performed by adjusting the respective relative positional relationship during assembling the both into the box body of the apparatus, however, only with such adjustment, once one of the units is detached from the box body of the apparatus for such as repairment and inspection, the prior positional relationship of both is destroyed and in order to reproduce the original positional relationship another readjustment is necessitated.

Therefore, two pieces of positioning pins for respective units are provided at the box body of the apparatus, and for both units corresponding guides which permit insertion of the respective positioning pins are provided. The positional relationship of these positioning pins is adjusted in advance in the box body of the apparatus and once such adjustment is performed, no readjustment thereof is required. Thus, even when one of the both units or the both units are detached from the box body of the apparatus, when attaching the same subsequently, if the units are attached along the positioning pins provided at the box body of the apparatus, the positional relationship of the both units can be reproduced without adjustment.

Now, a structure/jig (target, ruler, etc) of a calibration use device in the electrophoresis apparatus according to the present invention will be explained.

The auto sampler control unit which performs control for the auto sampler stores positional information (in X, Y and Z coordinate system) common between devices for moving the auto sampler and inserting the capillaries into such as the sampler plate and the buffer vessel. However, in an actual apparatus, the relative distance between the auto sampler and the capillary array finely varies device by device, therefore, the control unit performs correcting calculation of the positional information based on calibration value (offset value) stored for every device, and thereafter drives the auto sampler by making use of the coordinate system after the correction. The present apparatus is provided with a calibration function which determines the above calibration value, and the calibration value is stored for every apparatus in a built-in control PC for the apparatus while permitting rewriting thereof.

In the calibration of the auto sampler, a target 21 in a frust conical shape provided on the tray 5 in the auto sampler is determined as a reference position in X Y direction and a line 22 indicating the liquid surface in the buffer vessel to be attached to the tray 5 is determined as a reference position in Z direction, the auto sampler is moved to a position where the top ends of the capillaries coincide with these positions and the X, Y and Z coordinates of the auto sampler at this moment are stored as the calibration values. The coordinates of these reference positions are in advance stored in the auto sampler control unit and the positional coordinates of such as respective wells in the sample plate and the buffer vessel likely stored are determined based on the reference coordinates. Accordingly, through determination of difference between the calibration values determined by the calibration of the auto sampler and the coordinates of the reference positions for the calibration which are stored in advance in the control unit, the coordinates such as respective wells in the sample plate can be corrected.

Figure 10:
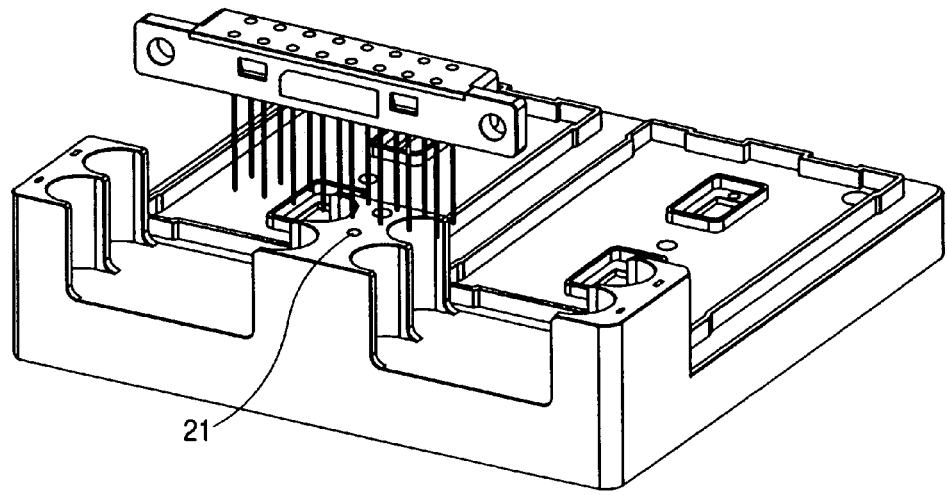
FIG. 10 is a perspective view for explaining a calibration function in X, Y directions according to the present invention.
Figure 11:
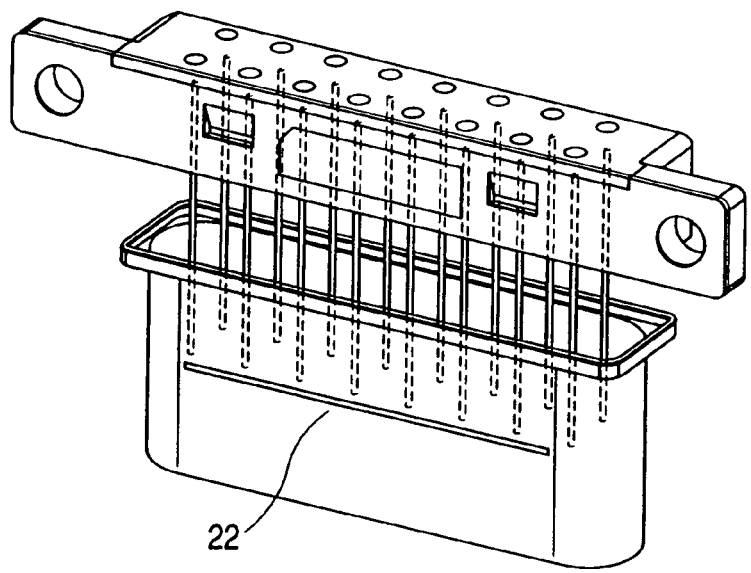
FIG. 11 is a perspective view for explaining a calibration function in Z direction according to the present invention.

Hereinbelow, the above calibration function will be explained in detail. FIG. 10 is a view for explaining a calibration in X Y direction and FIG. 11 is a view for explaining a calibration in Z direction. In the calibration in X Y direction, the auto sampler is moved to a position until the top end of the capillary coincides the target 21 on the tray 5 to thereby determine the calibration values in X Y direction. The capillary used for the calibration is one among the capillary array of 2×8 alignment which is on the front row seen from the front of the apparatus and at 4th from the right end. Principally, any capillaries can be used for the calibration, however, the above capillary is selected in view of easy to see from the operator.

Further, for the calibration in Z direction, the target line 22 (a line indicating amount of buffer liquid) printed on the buffer vessel as illustrated in FIG. 11 is used as the reference position, and the auto sampler is moved to a position until the top end of the capillary coincide with the line 22. Although, the tray 5 is omitted from FIG. 11, the calibration is performed by attaching the buffer vessel at a position of front left side of the tray 5. Not using a single reference point but dividing the reference positions into X Y direction and Z direction, a possible problem that during the calibration in X Y direction the top ends of the capillaries touch to the target 21 in the X Y direction is eliminated.

When the calibration of the auto sampler is performed in the manner as explained and the direction of the capillary array and the auto sampler is correctly adjusted, the capillary array correctly moves to all of the positions on the tray in the auto sampler. However, such is based on a precondition that 16 pieces of capillaries in the capillary array are correctly aligned in 2×8 matrix. Namely, the calibration of the auto sampler is performed by selecting one capillary among 16 pieces of capillaries as a representative, the remaining 15 pieces of capillaries have to be correctly aligned with respect to the one representative capillaries. However, it is possible that a person performing an analysis can by mistake bend a capillary during handling the capillary array, in such instance, it is indefinite whether all of the 16 pieces of the capillaries can be normally inserted into the corresponding wells in the sampler plate.

Figure 12:
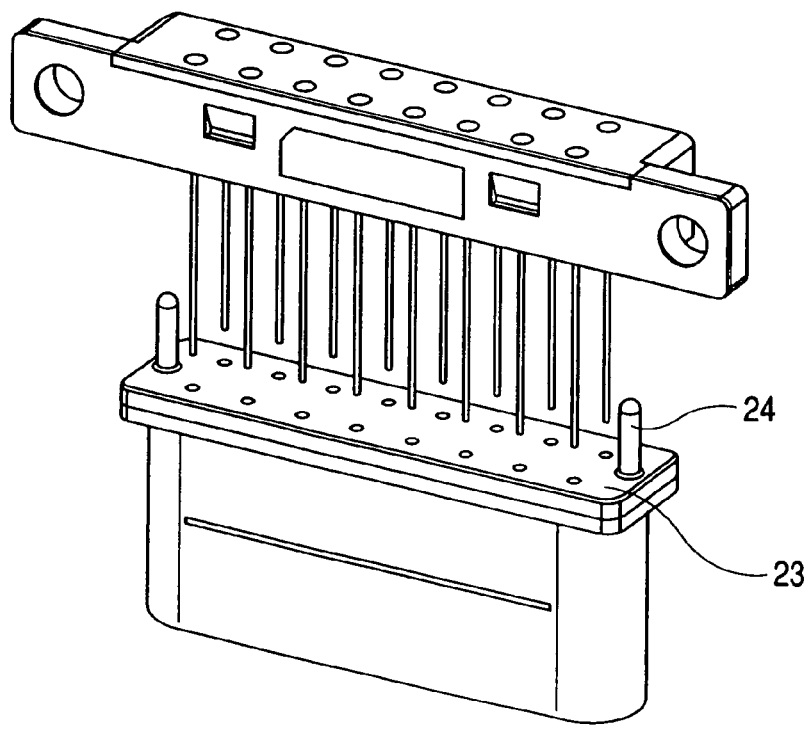
FIG. 12 is a perspective view for explaining a checking functions of capillary alignment in a capillary array according to the present invention.

Therefore, another function for checking whether the capillary which was bent by mistake by the person performing the analysis can be used as it is and whether the manually straightened capillary by the person can be used is necessitated. For this purpose, the present apparatus is further provided with an array checking function which performs the above checking. When performing the array checking function, a capillary array of which alignment is required to be checked is attached to the apparatus and after performing calibration of the auto sampler depending on necessity, the array target 23 for checking the alignment is attached on the buffer vessel as illustrated in FIG. 12 and the auto sampler is moved to a position where the buffer vessel comes immediately below the capillary array (in FIG. 12 the tray 5 is omitted like in FIG. 11).

A column 24 serves to lift the stopper plate (as shown in FIGS. 8A and 8B) which is located at the top ends of the capillaries when the array target 23 moves immediately below the capillary array so as to facilitate confirmation of the top end portion of the capillary array. The array target 23 is provided with 16 pieces of holes and these positional relationship is matched with the alignment interval of the capillary array. The diameter of the hole is determined as $\phi 2.0$ which is smaller than the minimum diameter of the well in the sample plate assembly as usually used, therefore, if the top ends of the capillaries located inside the outer circle of the respective holes in the array target 23, the capillary array can be inserted into the corresponding wells in the sample plate through movement of the auto sampler without damaging the capillary array. With this function a person performing an analysis can easily check the alignment of the capillary array.

According to the present invention, many number of samples can be automatically supplied to the capillaries.

The invention claimed is:

1. A capillary array electrophoretic device comprising:
   a capillary array comprising a plurality of capillaries having sample injection ends, said sample injection ends being arranged in order; and
   an autosampler for retaining a sample plate assembly comprising a microtiter plate having a plurality of wells capable of retaining a sample, said autosampler being movable at least in a first direction such that said sample injection ends of said capillary array can be immersed in said plurality of wells, and
   wherein said sample plate assembly comprises an adapter for mounting said microtiter plate and a septum holder capable of securing said microtiter plate to said adapter, and
   wherein said sample plate assembly is formed in a laminated structure, where said microtiter plate is stacked on said adapter, and septum holder is stacked on said microtiter plate.

2. The device of claim 1, further comprising a sensor for identifying one of a number and type of wells in said microtiter plate by detecting a shape of said sample plate assembly.

3. A capillary array electrophoretic device comprising:
   a capillary array comprising a plurality capillaries having sample injection ends, said sample injection ends being arranged in order; and
   an autosampler for retaining a sample plate assembly comprising a microtiter plate having a plurality of wells capable of retaining a sample, said autosampler being movable at least in a first direction such that said sample injection ends of said capillary array can be immersed in said plurality of wells, and
   wherein said sample plate assembly comprises an adapter for mounting said microtiter plate and a septum holder capable of securing said microtiter plate to said adapter,
   wherein said septum holder is capable of correcting said microtiter plate that has been deformed, and
   wherein said sample plate assembly is formed in a laminated structure, where said microtiter plate is stacked on said adapter, and said septum holder is stacked on said microtiter plate.

4. The device of claim 3, further comprising a sensor for identifying one of a number and type of wells in said microtiter plate by detecting a shape of said sample plate assembly.

* * * * *